United States Patent [19]

Hosaka et al.

[11] Patent Number: 5,498,770

[45] Date of Patent: Mar. 12, 1996

[54] CATALYST FOR THE POLYMERIZATION OF OLEFINS AND PROCESS FOR THE POLYMERIZATION OF OLEFINS

[75] Inventors: Motoki Hosaka; Kenji Goto; Masahiko Matsuo, all of Kanagawa, Japan

[73] Assignee: Toho Titanium Co., Ltd., Chigasaki, Japan

[21] Appl. No.: 309,885

[22] Filed: Sep. 20, 1994

[30] Foreign Application Priority Data

Apr. 28, 1994 [JP] Japan .................................. 6-113754

[51] Int. Cl.$^6$ .................................................... C08F 4/656
[52] U.S. Cl. ...................... 502/116; 502/112; 502/125; 502/127; 526/125.3; 526/128
[58] Field of Search ........................ 502/116, 125, 502/112, 127; 526/124, 128, 125.3

[56] References Cited

U.S. PATENT DOCUMENTS

| | | | |
|---|---|---|---|
| 4,816,433 | 3/1989 | Terano et al. | 502/127 |
| 5,354,820 | 10/1994 | Funabashi | 526/124 |

*Primary Examiner*—Romulo H. Delmendo

*Attorney, Agent, or Firm*—Oblon, Spivak, McClelland, Maier & Neustadt

[57] ABSTRACT

A catalyst for the polymerization of olefins comprising (A) a solid catalyst component essentially containing magnesium, titanium, an electron donor compound, and a halogen which is prepared by contacting a magnesium compound, a titanium halide compound, and an electron donor compound, (B) an organoaluminum compound, and (C) an organosilicon compound and a process for polymerizing an olefin using the same are disclosed, the organosilicon compound (C) being represented by formula (I):

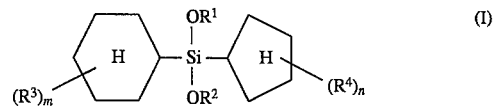

wherein $R^1$ and $R^2$, which may be the same or different, each represents an alkyl group having from 1 to 3 carbon atoms; $R^3$ and $R^4$, which may be the same or different, each represents an alkyl group having from 1 to 3 carbon atoms, or a halogen atom; and m and n each represents 0 or an integer of 1 or 2. A polyolefin having high stereoregularity and broad molecular weight distribution can be obtained in high yield.

9 Claims, No Drawings

CATALYST FOR THE POLYMERIZATION OF OLEFINS AND PROCESS FOR THE POLYMERIZATION OF OLEFINS

FIELD OF THE INVENTION

This invention relates to a catalyst for the polymerization of olefins and a process for the polymerization of olefins using the same. More particularly, it relates to a catalyst for the polymerization of olefins with which an olefin polymer having high stereoregularity and broad molecular weight distribution can be obtained in high yield and a process for polymerizing an olefin in the presence of the catalyst.

BACKGROUND OF THE INVENTION

For homo- or copolymerization of olefins a number of processes using a catalyst system comprising a solid catalyst component essentially containing magnesium, titanium, an electron donor compound, and a halogen, an organoaluminum compound, and an organosilicon compound have been proposed.

For example, JP-A-57-63310 (the term "JP-A" as used herein means an "unexamined published Japanese patent application") and JP-A-57-63311 propose a process for polymerizing an olefin having 3 or more carbon atoms using a catalyst system comprising a solid catalyst component containing a magnesium compound, a titanium compound and an electron donor, an organoaluminum compound, and an organosilicon compound having an Si-O-C bond. However, these processes are not always satisfactory for obtaining highly stereoregular polymers in high yield, and further improvement has been demanded.

On the other hand, JP-A-63-3010 discloses a catalyst system for the polymerization of olefins and a process for polymerizing olefins using the same, the catalyst system comprising (a) a solid catalyst component prepared by bringing a dialkoxymagnesium, a diester of aromatic dicarboxylic acid, an aromatic hydrocarbon, and a titanium halide into contact and subjecting the resulting product in a powdered state to a heat treatment, (b) an organoaluminum compound, and (c) an organosilicon compound.

JP-A-1-315406 discloses a catalyst system for olefin polymerization and a process for polymerizing an olefin using the same, the catalyst system comprising (a) a solid catalyst component prepared by bringing titanium tetrachloride into contact with a suspension of diethoxymagnesium in an alkylbenzene, adding phthalic acid dichloride thereto to react to obtain a solid product, and further contacting the resulting solid product with titanium tetrachloride in the presence of an alkylbenzene, (b) an organoaluminum compound, and (c) an organosilicon compound.

JP-A-2-84404 proposes a catalyst system for the polymerization of olefins and a process for homo- or copolymerizing an olefin(s) using the same, the catalyst system comprising (a) a solid titanium catalyst component essentially containing magnesium, titanium and a halogen which is prepared by bringing a magnesium compound and a titanium compound into contact, (b) an organoaluminum compound catalyst component, and (c) an organosilicon compound catalyst component containing a cyclopentyl group or a derivative thereof, a cyclopentenyl group or a derivative thereof, or a cyclopentadienyl group or a derivative thereof.

Each of these known techniques aims at such high catalytic activity that a step of removing residual catalyst components, such as chlorine and titanium, from the resulting polymer (a so-called ashing step) may be omitted and, at the same time, an improvement in yield of a stereoregular polymer or an improvement in durability of the catalytic activity for polymerization, and has achieved excellent results to their purpose.

In recent years, however, it has been pointed out that the olefin polymers obtained by polymerization using these catalyst systems comprising such a highly active catalyst component, an organoaluminum compound and an organosilicon compound have narrower molecular weight distribution as compared with those obtained by using conventional catalyst systems comprising a titanium trichloride type catalyst component in combination with an organoaluminum compound and, if desired, an electron donor compound as a third component. For polyolefins to have narrower molecular weight distribution means poorer moldability, leading to less applicability.

Various manipulations have been suggested to solve this problem. For example, adoption of a multi-stage polymerization system has been proposed for obtaining polyolefins with broader molecular weight distribution. Nevertheless, a multi-stage polymerization system requires repetition of tedious and complicated operation of polymerization and also involves a step for recovery of a chelating agent to be used for polymerization and is not therefore deemed to be favorable from the considerations of labor and cost.

As the latest technique, JP-A-3-7703 discloses a process for polymerizing an olefin in the presence of a catalyst system comprising (a) a solid titanium catalyst component essentially containing magnesium, titanium, a halogen, and an electron donor, (b) an organoaluminum compound, and (c) at least two organosilicon compounds as an electron donor. According to this process, a polyolefin having broad molecular weight distribution can be obtained without involving laborious multi-stage polymerization operation. However, the use of at least two organosilicon compounds as an electron donor for polymerization makes the process still tedious and complicated.

SUMMARY OF THE INVENTION

An object of the present invention is to provide a catalyst for the polymerization of olefins which can eliminate the above-mentioned problems associated with the conventional techniques, i.e., a catalyst which exhibits high polymerization activity through simpler operation and provides an olefin polymer having broad molecular weight distribution while maintaining a satisfactory yield of a highly stereoregular polymer.

Another object of the present invention is to provide a process for polymerizing an olefin to produce a polyolefin having broad molecular weight distribution and high stereoregularity in high yield.

As a result of extensive investigations, the present inventors have found that an olefin polymer having high stereoregularity and broad molecular weight distribution can be obtained in high yield by polymerizing an olefin(s) in the presence of a catalyst comprising (A) a solid catalyst component essentially containing magnesium, titanium, an electron donor compound, and a halogen, which is formed by bringing a magnesium compound, a titanium halide compound, and an electron donor compound into contact, (B) an organoaluminum compound, and (C) an organosilicon compound having a specific structure. The present invention has been completed based on this finding.

The present invention provides a catalyst for the polymerization of olefins comprising (A) a solid catalyst component essentially containing magnesium, titanium, an electron donor compound, and a halogen, which is prepared by bringing a magnesium compound, a titanium halide compound, and an electron donor compound into contact, (B) an organoaluminum compound, and (C) an organosilicon compound represented by formula (I):

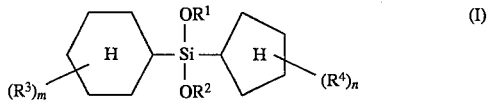

wherein $R^1$ and $R^2$, which may be the same or different, each represent an alkyl group having from 1 to 3 carbon atoms; $R^3$ and $R^4$, which may be the same or different, each represents an alkyl group having from 1 to 3 carbon atoms or a halogen atom; and m and n each represents 0 or an integer of 1 or 2.

DETAILED DESCRIPTION OF THE INVENTION

Solid catalyst component (A), which constitutes the catalyst for the polymerization of olefins according to the present invention, is prepared by contacting a magnesium compound, a titanium halide compound, and an electron donor compound and contains magnesium, titanium, an electron donor compound and a halogen as essential components.

The magnesium compound which can be used for preparing solid catalyst component (A) includes metallic magnesium, a magnesium dihalide, a dialkylmagnesium, an alkylmagnesium halide, a dialkoxymagnesium, a diaryloxymagnesium, and an alkoxymagnesium halide. The alkyl or alkoxy moiety of the above-described magnesium compounds generally has from 1 to 6 carbon atoms and preferably from 1 to 4 carbon atoms.

Specific examples of the magnesium halide are magnesium dichloride, magnesium dibromide, magnesium diiodide, and magnesium difluoride.

Specific examples of the dialkylmagnesium are dimethylmagnesium, diethylmagnesium, ethylmethylmagnesium, dipropylmagnesium, methylpropylmagnesium, ethylpropylmagnesium, dibutylmagnesium, butylmethylmagnesium, and butylethylmagnesium. These dialkylmagnesiums may be obtained by reacting metallic magnesium with a halogenated hydrocarbon or an alcohol.

Specific examples of the alkylmagnesium halide include ethylmagnesium chloride, propylmagnesium chloride, and butylmagnesium chloride. These alkylmagnesium halides may be obtained by reacting metallic magnesium with a halogenated hydrocarbon or an alcohol.

Specific examples of the dialkoxymagnesium and the diaryloxymagnesium include dimethoxymagnesium, diethoxymagnesium, dipropoxymagnesium, dibutoxymagnesium, diphenoxymagnesium, ethoxymethoxymagnesium, ethoxypropoxymagnesium, and butoxyethoxymagnesium.

Specific examples of the alkoxymagnesium halide are methoxymagnesium chloride, ethoxymagnesium chloride, propoxymagnesium chloride, and butoxymagnesium chloride.

Preferred of these magnesium compounds are dialkoxymagnesiums, with diethoxymagnesium and dipropoxymagnesium being especially preferred. The magnesium compounds may be used either individually or in combination of two or more thereof.

The dialkoxymagnesium, which can be used preferably, is at least one dialkoxymagnesium species having from 1 to 3 carbon atoms in the alkoxy moiety thereof and has a granular or powdered form, the particles of which may have an irregular shape or a spherical shape. In using spherical particles of diethoxymagnesium, the resulting powdered polymer will have a more satisfactory particle shape and a narrower particle size distribution. As a result, the polymer powder as produced has improved handling properties, and troubles attributed to fine particles, such as obstruction, would be eliminated.

The spherical diethoxymagnesium particles as above referred to do not necessarily need to be true spheres, and ellipsoidal or potato-like particles may also be used. The terminology "spherical" as used herein may be quantified as a longer axis diameter (l) to shorter axis diameter (w) ratio (l/w) of not more than 3, preferably from 1 to 2, and still preferably from 1 to 1.5.

The dialkoxymagnesium to be used has an average particle size of from 1 to 200 μm, preferably from 5 to 150 μm.

In the case of spherical diethoxymagnesium, it has an average particle size of from 1 to 100 μm, preferably from 5 to 50 μm, more preferably from 10 to 40 μm. It is preferable to use particles having a sharp size distribution with a small proportion of fine or coarse particles. More specifically, particles containing not more than 20%, preferably not more than 10%, of fine particles of 5 μm or smaller and not more than 10%, preferably not more than 5%, of coarse particles of 100 μm or greater. Such a particle size distribution corresponds to in ($D_{90}/D_{10}$) of not more than 3, preferably not more than 2, wherein $D_{90}$ and $D_{10}$ represent a cumulative 90% diameter and a cumulative 10% diameter, respectively, of a cumulative particle size distribution depicted from the small diameter side.

The above-mentioned dialkoxymagnesium does not always need to be present as a starting material in the preparation of solid catalyst component (A). For example, it may be prepared in situ from metallic magnesium and an alcohol in the presence of a catalyst, e.g., iodine at the time of preparing solid catalyst component (A).

The titanium halide compound which can be used for preparing solid catalyst component (A) is at least one of a titanium halide and an alkoxytitanium halide represented by formula: $Ti(OR^5)_nX_{4-n}$, wherein $R^5$ represents an alkyl group having from 1 to 4 carbon atoms; X represents a chlorine atom, a bromine atom or an iodine atom; and n represents 0 or an integer of 1, 2 or 3.

Specific examples of the titanium halide include titanium tetrahalides, such as $TiCl_4$, $TiBr_4$, and $TiI_4$. Specific examples of the alkoxytitanium halide are $Ti(OCH_3)Cl_3$, $Ti(OC_2H_5)Cl_3$, $Ti(OC_3H_7)Cl_3$, $Ti(On-C_4H_9)Cl_3$, $Ti(OCH_3)_2Cl_2$, $Ti(OC_2H_5)_2Cl_2$, $Ti(OC_3H_7)_2Cl_2$, $Ti(On-C_4H_9)_2Cl_2$, $Ti(OCH_3)_3Cl$, $Ti(OC_2H_5)_3Cl$, $Ti(OC_3H_7)_3Cl$, and $Ti(On-C_4H_9)_3Cl$. Preferred of these titanium halide compounds are titanium tetrahalides, with $TiCl_4$ being particularly preferred. These titanium halide compounds may be used either individually or in combination of two or more thereof.

The electron donor compound which can be used for preparing solid catalyst component (A) is an organic compound containing oxygen or nitrogen. Such a compound include alcohols, phenols, ethers, esters, ketones, acid halides, aldehydes, amines, amides, nitriles, isocyanates, and organosilicon compounds containing an Si-O-C bond.

Specific examples of the electron donor compound include alcohols, such as methanol, ethanol, propanol, butanol, pentanol, hexanol, octanol, 2-ethylhexyl alcohol, and dodecanol; phenols, such as phenol and cresol; ethers, such as dimethyl ether, diethyl ether, dipropyl ether, dibutyl ether, diamyl ether, and diphenyl ether; monocarboxylic acid esters, such as methyl formate, ethyl acetate, vinyl acetate, propyl acetate, octyl acetate, cyclohexyl acetate, ethyl propionate, ethyl butyrate, methyl benzoate, ethyl benzoate, propyl benzoate, butyl benzoate, octyl benzoate, cyclohexyl benzoate, phenyl benzoate, methyl p-toluylate, ethyl p-toluylate, methyl anisate, and ethyl anisate; dicarboxylic acid esters, such as diethyl maleate, dibutyl maleate, dimethyl adipate, diethyl adipate, dipropyl adipate, dibutyl adipate, dimethyl adipate, diisodecyl adipate, dioctyl adipate, dimethyl phthalate, diethyl phthalate, dipropyl phthalate, dibutyl phthalate, dipentyl phthalate, dihexyl phthalate, diheptyl phthalate, dioctyl phthalate, dinonyl phthalate, and didecyl phthalate; ketones, such as acetone, methyl ethyl ketone, methyl butyl ketone, acetophenone, and benzophenone; acid halides, such as phthalic acid dichloride and terephthalic acid dichloride; aldehydes, such as acetaldehyde, propionaldehyde, octylaldehyde, and benzaldehyde; amines, such as methylamine, ethylamine, tributylamine, piperidine, aniline, and pyridine; amides, such as acetamide, and acrylamide; nitriles, such as acetonitrile, benzonitrile, and tolunitrile; and isocyanates, such as phenyl isocyanate, and n-butyl isocyanate.

Specific examples of the organosilicon compound containing an Si-O-C bond are trimethylmethoxysilane, trimethylethoxysilane, tri-n-propylmethoxysilane, tri-n-propylethoxysilane, tri-n-butylmethoxysilane, tri-isobutylmethoxysilane, tri-t-butylmethoxysilane, tri-n-butylethoxysilane, tricyclohexylmethoxysilane, tricyclohexylethoxysilane, dimethyldimethoxysilane, dimethyldiethoxysilane, di-n-propyldimethoxysilane, diisopropyldimethoxysilane, di-n-propyldiethoxysilane, diisopropyldiethoxysilane, di-n-butyldimethoxysilane, diisobutyldimethoxysilane, di-t-butyldimethoxysilane, di-n-butyldiethoxysilane, n-butylmethyldimethoxysilane, bis(2-ethylhexyl)dimethoxysilane, bis(2-ethylhexyl)diethoxysilane, dicyclohexyldimethoxysilane, dicyclohexyldiethoxysilane, dicyclopentyldimethoxysilane, dicyclopentyldiethoxysilane, cyclohexylmethyldimethoxysilane, cyclohexylmethyldiethoxysilane, cyclohexylethyldimethoxysilane, cyclohexylisopropyldimethoxysilane, cyclohexylethyldiethoxysilane, cyclopentylmethyldimethoxysilane, cyclopentylethyldiethoxysilane, cyclopentylisopropyldimethoxysilane, cyclohexyl(n-pentyl)dimethoxysilane, cyclopentylisobutyldimethoxysilane, diphenyldimethoxysilane, diphenyldiethoxysilane, phenylmethyldimethoxysilane, phenylmethyldiethoxysilane, phenylethyldimethoxysilane, phenylethyldiethoxysilane, cyclohexyldimethylmethoxysilane, cyclohexyldimethylethoxysilane, cyclohexyldiethylmethoxysilane, cyclohexyldiethylethoxysilane, 2-ethylhexyltrimethoxysilane, 2-ethylhexyltriethoxysilane, cyclohexyl(n-pentyl)diethoxysilane, cyclopentylmethyldimethoxysilane, cyclopentylethyldimethoxysilane, cyclopentylmethyldiethoxysilane, cyclopentylethyldiethoxysilane, cyclohexyl(n-propyl)dimethoxysilane, cyclo-hexyl(n-butyl)dimethoxysilane, cyclohexyl(n-propyl)diethoxysilane, cyclohexyl(n-butyl)diethoxysilane, methyltrimethoxysilane, methyltriethoxysilane, ethyltrimethoxysilane, ethyltriethoxysilane, n-propyltrimethoxysilane, n-propyltriethoxysilane, isopropyltrimethoxysilane, isopropyltriethoxysilane, n-butyltrimethoxysilane, isobutyltrimethoxysilane, t-butyltrimethoxysilane, n-butyltriethoxysilane, cyclohexyltrimethoxysilane, cyclohexyltriethoxysilane, cyclopentyltrimethoxysilane, cyclopentyltriethoxysilane, vinyltrimethoxysilane, vinyltriethoxysilane, 2-ethylhexyltrimethoxysilane, 2-ethylhexyltriethoxysilane, phenyltrimethoxysilane, and phenyltriethoxysilane.

Among these electron donor compounds preferred are esters, with phthalic diesters being more preferred. The ester moiety in the phthalic diesters is preferably a straight chain or branched chain alkyl group having from 1 to 12 carbon atoms and preferably from 2 to 10 carbon atoms. Specific examples of suitable phthalic diesters are dimethyl phthalate, diethyl phthalate, di-n-propyl phthalate, diisopropyl phthalate, di-n-butyl phthalate, diisobutyl phthalate, ethylmethyl phthalate, methylisopropyl phthalate, ethyl-n-propyl phthalate, ethyl-n-butyl phthalate, di-n-pentyl phthalate, diisopentyl phthalate, dihexyl phthalate, di-n-heptyl phthalate, di-n-octyl phthalate, bis(2-methylhexyl)phthalate, bis(2-ethylhexyl)phthalate, di-n-nonyl phthalate, diisodecyl phthalate, bis(2,2-dimethylheptyl) phthalate, n-butylisohexyl phthalate, n-butylisooctyl phthalate, n-pentylhexyl phthalate, n-pentylisohexyl phthalate, isopentylheptyl phthalate, n-pentylisooctyl phthalate, n-pentylisononyl phthalate, isopentyl-n-decyl phthalate, n-pentylundecyl phthalate, isopentylisohexyl phthalate, n-hexylisooctyl phthalate, n-hexylisononyl phthalate, n-hexyl-n-decyl phthalate, n-heptylisooctyl phthalate, n-heptylisononyl phthalate, n-heptylneodecyl phthalate, and isooctylisononyl phthalate. These phthalic acid esters may be used either individually or in combination of two or more thereof. The preferred combination of the phthalic acid esters is exemplified with: diethyl phthalate and bis(2-ethylhexyl) phthalate; di-n-butyl phthalate and bis(2-ethylhexyl) phthalate; diisobutyl phthalate and bis(2-ethylhexyl) phthalate; and diethyl phthalate, bis(2-ethylhexyl) phthalate and di-n-butyl phthalate.

Solid catalyst component (A) can be prepared by contacting the above-mentioned magnesium compound, titanium halide compound and electron donor compound in a manner appropriately selected from conventional means. Known methods for preparing a solid catalyst component are disclosed, e.g., in JP-A-63-308004, JP-A-63-314211, JP-A-64-6006, JP-A-64-14210, JP-A-64-43506, JP-A-63-3010, and JP-A-62-158704.

Typical methods for preparing solid catalyst component (A) are described below.

(1) Magnesium chloride is dissolved in a tetraalkoxytitanium, and the solution is brought into contact with polysiloxane to obtain a solid component. The solid component is reacted with silicon tetrachloride, contacted with phthalic acid dichloride, and reacted with titanium tetrachloride to prepare solid catalyst component (A). The resulting solid catalyst component may be preliminarily treated with an organoaluminum compound, an organosilicon compound, and an olefin.

(2) Anhydrous magnesium chloride and 2-ethylhexyl alcohol are reacted to form a uniform solution, which is brought into contact with phthalic anhydride. The resulting solution is then brought into contact with titanium tetrachloride and diester of phthalic acid to obtain a solid component, which is further reacted with titanium tetrachloride to prepare solid catalyst component (A).

(3) Metallic magnesium, butyl chloride, and butyl ether are reacted to synthesize an organomagnesium compound. The organomagnesium compound is brought into contact with tetrabutoxytitanium and tetraethoxysilane to obtain a solid product, which is then brought into contact with a diester (e.g., an alkyl ester having 1 to 10 carbon atoms) of phthalic acid, dibutyl ether, and titanium tetrachloride to prepare solid catalyst component (A). The resulting solid catalyst component may be preliminarily treated with an organoaluminum compound, an organosilicon compound, and an olefin.

(4) An organomagnesium compound, e.g., dibutylmagnesium, and an organoaluminum compound are brought into contact with an alcohol, e.g., butanol or 2-ethylhexyl alcohol, in the presence of a hydrocarbon solvent to form a uniform solution. The resulting solution is brought into contact with a silicon compound, e.g., $SiCl_4$, $HSiCl_3$ or polysiloxane, to obtain a solid component. The solid component is brought into contact with titanium tetrachloride and a diester of phthalic acid in the presence of an aromatic hydrocarbon solvent, and the reaction mixture is further brought into contact with titanium tetrachloride to obtain solid catalyst component (A).

(5) Magnesium chloride, a tetraalkoxytitanium, and an aliphatic alcohol are brought into contact in the presence of an aliphatic hydrocarbon to form a uniform solution. Titanium tetrachloride is added to the solution, and the mixture is heated to precipitate a solid component. The solid component is contacted with a diester of phthalic acid and further reacted with titanium tetrachloride to prepare solid catalyst component (A).

(6) Metallic magnesium powder, an alkyl monohalide, and iodine are contacted. The resulting reaction product, a tetraalkoxytitanium, an acid halide, and an aliphatic alcohol are contacted in the presence of an aliphatic hydrocarbon to form a uniform solution. Titanium tetrachloride is added to the solution, and the mixture is heated to precipitate a solid component. The solid component is brought into contact with a diester of phthalic acid and further reacted with titanium tetrachloride to prepare solid catalyst component (A).

(7) Diethoxymagnesium is suspended in an alkylbenzene or a halogenated hydrocarbon solvent, and the resulting suspension is brought into contact with titanium tetrachloride. The mixture is heated and then contacted with a diester (e.g., an alkyl ester having 1 to 10 carbon atoms) of phthalic acid to obtain a solid component. The solid component is washed with an alkylbenzene and again contacted with titanium tetrachloride in the presence of the alkylbenzene to prepare solid catalyst component (A). The resulting solid catalyst component may be subjected to a heat treatment in the presence or absence of a hydrocarbon solvent.

(8) Diethoxymagnesium is suspended in an alkylbenzene, and the resulting suspension is brought into contact with titanium tetrachloride and phthalic acid chloride to obtain a solid component. The solid component is washed with an alkylbenzene and again contacted with titanium tetrachloride in the presence of the alkylbenzene to prepare solid catalyst component (A). The resulting solid catalyst component may further be contacted with titanium tetrachloride twice or more times.

(9) Diethoxymagnesium, calcium chloride, and a silicon compound represented by $Si(OR^6)_4$ (wherein $R^6$ is an alkyl group or an aryl group) are co-ground, and the resulting grinds are suspended in an aromatic hydrocarbon. The suspension is brought into contact with titanium tetrachloride and an diester (e.g., an alkyl ester having 1 to 10 carbon atoms) of phthalic acid, and the product is further contacted with titanium tetrachloride to prepare solid catalyst component (A).

(10) Diethoxymagnesium and a diester of phthalic acid are suspended in an alkylbenzene, and the suspension is added to titanium tetrachloride to obtain a solid component. The solid component is washed with an alkylbenzene, and further contacted with titanium tetrachloride in the presence of the alkylbenzene to prepare solid catalyst component (A).

(11) A calcium halide and aliphatic magnesium, e.g., magnesium stearate, are contact reacted with titanium tetrachloride and a diester (e.g., an alkyl ester having 1 to 10 carbon atoms) of phthalic acid, and the reaction product is further brought into contact with titanium tetrachloride to prepare solid catalyst component (A).

(12) Diethoxymagnesium is suspended in an alkylbenzene or a halogenated hydrocarbon solvent, and the resulting suspension is brought into contact with titanium tetrachloride, and the mixture is heated and contacted with a diester (e.g., an alkyl ester having 1 to 10 carbon atoms) of phthalic acid to react. The resulting solid component is washed with an alkylbenzene and further contacted with titanium tetrachloride in the presence of the alkylbenzene to prepare solid catalyst component (A). At any stage of the above preparation procedure, the system may be brought into contact with aluminum chloride.

(13) Diethoxymagnesium is suspended in an alkylbenzene or a halogenated hydrocarbon solvent, and the resulting suspension is brought into contact with titanium tetrachloride, and the mixture is heated and contacted with two or more diesters of phthalic acid different in the carbon atom number of the alkyl moiety (e.g., diethyl phthalate and bis(2-ethyhexyl) phthalate) to obtain a solid component. The resulting solid component is washed with an alkylbenzene and further contacted with titanium tetrachloride in the presence of the alkylbenzene to prepare solid catalyst component (A). In the above preparation, when the solid component is brought into contact with titanium tetrachloride, it may again contacted with two or more diesters of phthalic acid different in the carbon atom number of the alkyl moiety. Further, the diesters of phthalic acid may be used in combination with the above-enumerated electron donor compound other than diesters of phthalic acid.

(14) Diethoxymagnesium, titanium tetrachloride, and a diester of phthalic acid are brought into contact in the presence of chlorobenzene, and the reaction product is then contacted with titanium tetrachloride and phthalic acid dichloride. The product is further contact reacted with titanium tetrachloride to prepare solid catalyst component (A). The thus prepared solid catalyst component may further be contacted with titanium tetrachloride. Further, at any stage of the above preparation procedure, a silicon compound may be contacted with the preparation system.

(15) Diethoxymagnesium, 2-ethylhexyl alcohol, and carbon dioxide are brought into contact in the presence of toluene to form a uniform solution. The solution is contacted with titanium tetrachloride and a diester of phthalic acid to obtain a solid component. The solid component is dissolved in tetrahydrofuran, and the solid component is made to precipitate. The resulting solid component is contact reacted with titanium tetrachloride to prepare solid catalyst component. If desired, the contact with titanium tetrachloride may be conducted repeatedly. At any stage of the above preparation procedure, a silicon compound, e.g., tetrabutoxysilane, may be contacted with the preparation system.

The amounts of the magnesium compound, titanium halide compound and electron donor compound to be used for the preparation of solid catalyst component (A) vary depending on the method of preparation and cannot be generally specified. For example, the titanium halide compound is used in an amount of from 0.5 to 100 mol, preferably from 1 to 10 mol, and the electron donor compound from 0.01 to 3 mol, preferably from 0.02 to 1 mol, each per mole of the magnesium compound. The titanium content in solid catalyst component (A) is not particularly limited and it is generally from 0.5 to 10 % by weight, preferably from 1 to 5 % by weight, based on the weight of solid catalyst component (A).

Organoaluminum compound (B) which can be used in the present invention includes compounds represented by general formula: $R^7_y AlY_{3-y}$, wherein $R^7$ represents an alkyl group having from 1 to 4 carbon atoms; Y represents a hydrogen atom, a chlorine atom, a bromine atom or an iodine atom; and y represents an integer of 1, 2 or 3.

Specific examples of organoaluminum compound (B) are triethylaluminum, diethylaluminum chloride, triisobutylaluminum, diethylaluminum bromide, and diethylaluminum hydride. These organoaluminum compounds may be used either individually or in combination of two or more thereof. Preferred of them are triethylaluminum and triisobutylaluminum.

Organosilicon compound (C) which can be used in the present invention includes compounds represented by formula (I):

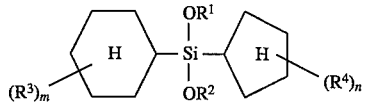

wherein $R^1$ and $R^2$, which may be the same or different, each represents an alkyl group having from 1 to 3 carbon atoms; $R^3$ and $R^4$, which may be the same or different, each represents an alkyl group having from 1 to 3 carbon atoms, or a halogen atom; and m and n each represent 0 or an integer of 1 or 2.

That is, organosilicon compound (C) is an asymmetric organosilicon compound having a cyclohexyl group or a derivative thereof and a cyclopentyl group or a derivative thereof both directly bonded to the silicon atom.

A combined use of such specific organosilicon compound (C) with solid catalyst component (A) and organoaluminum compound (B) makes it possible to produce an olefin polymer having markedly higher stereoregularity and broader molecular weight distribution in higher yield than in using conventional catalysts.

Specific examples of the asymmetric organosilicon compound (C) include cyclohexylcyclopentyldimethoxysilane, cyclohexylcyclopentyldiethoxysilane, and cyclohexylcyclopentyldipropoxysilane.

Various derivatives of these asymmetric organosilicon compounds are included within the scope of formula (I). In particular, those having one or two substituents ($R^3$), such as a methyl group, chlorine or bromine, at the 3-, 4- or 5-position of the cyclohexyl group thereof and/or one or two substituents ($R^4$) as exemplified above at the 2-, 3- or 5-position of the cyclopentyl group thereof are preferred. Two substituents may be at the same position of the cyclohexyl or cyclopentyl group. When m or n in formula (I) is 2, plurality of the substituent $R^3$ or $R^4$ may be the same or different.

Specific examples of the derivatives of the asymmetric organosilicon compounds are. 3-methylcyclohexylcyclopentyldimethoxysilane, 3-methylcyclohexylcyclopentyldiethoxysilane, 3-methylcyclohexylcyclopentyldipropoxysilane, 4-methylcyclohexylcyclopentyldimethoxysilane, 4-methylcyclohexylcyclopentyldiethoxysilane, 4-methylcyclohexylcyclopentyldipropoxysilane, 3,5-dimethylcyclohexylcyclopentyldimethoxysilane, 3,5-dimethylcyclohexylcyclopentyldiethoxysilane, 3,5-dimethylcyclohexylcyclopentyldipropoxysilane, 3,3-dimethylcyclohexylcyclopentyldimethoxysilane, 4,4-dimethylcyclohexylcyclopentyldimethoxysilane, cyclohexyl-2-methylcyclopentyldimethoxysilane, cyclohexyl-2-methylcyclopentyldiethoxysilane, cyclohexyl-2-methylcyclopentyldipropoxysilane, 3-methylcyclohexyl-2-methylcyclopentyldimethoxysilane, 3-methylcyclohexyl-2-methylcyclopentyldiethoxysilane, 3-methylcyclohexyl-2-methylcyclopentyldipropoxysilane, 4-methylcyclohexyl-2-methylcyclopentyldimethoxysilane, 4-methylcyclohexyl-2-methylcyclopentyldiethoxysilane, 4-methylcyclohexyl-2-methylcyclopentyldipropoxysilane, 3,5-dimethylcyclohexyl-2-methylcyclopentyldimethoxysilane, 3,5-dimethylcyclohexyl-2-methylcyclopentyldiethoxysilane, 3,5-dimethylcyclohexyl-2-methylcyclopentyldipropoxysilane, 3,3-dimethylcyclohexyl-2-methylcyclopentyldimethoxysilane, 4,4-dimethylcyclohexyl-2-methylcyclopentyldimethoxysilane, cyclohexyl-3-methylcyclopentyldimethoxysilane, cyclohexyl-3-methylcyclopentyldiethoxysilane, cyclohexyl-3-methylcyclopentyldipropoxysilane, 3-methylcyclohexyl-3-methylcyclopentyldimethoxysilane, 3-methylcyclohexyl-3-methylcyclopentyldiethoxysilane, 3-methylcyclohexyl-3-methylcyclopentyldipropoxysilane, 4-methylcyclohexyl-3-methylcyclopentyldimethoxysilane, 4-methylcyclohexyl-3-methylcyclopentyldiethoxysilane, 4-methylcyclohexyl-3-methylcyclopentyldipropoxysilane, 3,5-dimethylcyclohexyl-3-methylcyclopentyldimethoxysilane, 3,5-dimethylcyclohexyl-3-methylcyclopentyldiethoxysilane, 3,5-dimethylcyclohexyl-3-methylcyclopentyldipropoxysilane, 3,3-dimethylcyclohexyl-3-methylcyclopentyldimethoxysilane, 4,4-dimethylcyclohexyl-3-methylcyclopentyldimethoxysilane, cyclohexyl-2,3-dimethylcyclopentyldimethoxysilane, cyclohexyl-2,3-dimethylcyclopentyldiethoxysilane, cyclohexyl-2,3-dimethylcyclopentyldipropoxysilane, 3-methyl-cyclohexyl-2,3-dimethylcyclopentyldimethoxysilane, 3-methyl-cyclohexyl-2,3-dimethylcyclopentyldiethoxysilane, 3-methyl-cyclohexyl-2,3-dimethylcyclopentyldipropoxysilane, 4-methyl-cyclohexyl-2,3-dimethylcyclopentyldimethoxysilane,
4-methyl-cyclohexyl-2,3-dimethylcyclopentyldiethoxysilane,
4-methyl-cyclohexyl-2,3-dimethylcyclopentyldipropoxysilane, 3,5-dimethylcyclohexyl-2,3-dimethylcyclopentyldimethoxysilane, 3,5dimethylcyclohexyl -2,3-dimethylcyclopentyldiethoxysilane, 3,5-dimethylcyclohexyl-2,3-dimethylcyclopentyldipropoxysilane, 3,3-dimethylcyclohexyl-2,3-dimethylcyclopentyldimethoxysilane, 4,4-dimethylcyclohexyl-2,3-dimethylcyclopentyldimethoxysilane, cyclohexyl-2,5-dimethylcyclopentyldimethoxysilane, cyclohexyl2,5-dimethylcyclopentyldiethoxysilane, cyclohexyl-2,5-dimethylcyclopentyldipropoxysilane, 3-methylcyclohexyl-2,5-dimethylcyclopentyldimethoxysilane, 3-methylcyclohexyl-2,5-dimethylcyclopentyldiethoxysilane, 3-methylcyclohexyl-2,5-dimethylcyclopentyldipropoxysilane, 4-methylcyclohexyl-2,5-dimethylcyclopentyldimethoxysilane, 4-methylcyclohexyl-2,5-dimethylcyclopentyldiethoxysilane, 4-methylcyclohexyl-2,5-dimethylcyclopentyldipropoxysilane, 3,5-dimethylcyclohexyl-2,5-dimethylcyclopentyldimethoxysilane, 3,5-dimethylcyclohexyl-2,5-dimethylcyclopentyldiethoxysilane,3,5dimethylcyclohexyl 2,5-dimethylcyclopentyldipropoxysilane, 3,3-dimethylcyclohexyl-2,5-dimethylcyclopentyldimethoxysilane, 4,4-dimethylcyclohexyl-2,5-dimethylcyclopentyldimethoxysilane, cyclohexyl-2,2-dimethylcyclopentyldimethoxysilane, cyclohexyl-2,2-dimethylcyclopentyl diethoxysilane, cyclohexyl-2,2-dimethylcyclopentyldipropoxysilane, 3-methylcyclohexyl-2,2-dimethylcyclopentyldimethoxysilane, 3-methylcyclohexyl-2,2-dimethylcyclopentyldiethoxysilane, 3-methylcyclohexyl-2,2-dimethylcyclopentyldipropoxysilane, 4-methylcyclohexyl-2,2-dimethylcyclopentyldimethoxysilane, 4-methylcyclohexyl-2,2-dimethylcyclopentyldiethoxysilane, 4-methylcyclohexyl-2,2-dimethylcyclopentyldipropoxysilane, 3,5-dimethylcyclohexyl-2,2-dimethylcyclopentyldimethoxysilane, 3,5-dimethylcyclohexyl-2,2-dimethylcyclopentyldiethoxysilane, 3,5-dimethylcyclohexyl-2,2-dimethylcyclopentyldipropoxysilane, 3,3-dimethylcyclohexyl-2,2-dimethylcyclopentyldimethoxysilane, 4,4-dimethylcyclohexyl-2,2-dimethylcyclopentyldimethoxysilane, cyclohexyl-3,3-dimethylcyclopentyldimethoxysilane, cyclohexyl-3,3-dimethylcyclopentyldiethoxysilane, cyclohexyl-3,3-dimethylcyclopentyldipropoxysilane, 3-methylcyclohexyl-3,3-dimethylcyclopentyldimethoxysilane, 3-methylcyclohexyl-3,3-dimethylcyclopentyldiethoxysilane, 3-methylcyclohexyl-3,3-dimethylcyclopentyldipropoxysilane, 4-methylcyclohexyl-3,3-dimethylcyclopentyldimethoxysilane, 4-methylcyclohexyl-3,3-dimethylcyclopentyldiethoxysilane, 4-methylcyclohexyl-3,3-dimethylcyclopentyldipropoxysilane, 3,5-dimethylcyclohexyl-3,3-dimethylcyclopentyldimethoxysilane, 3,5-dimethylcyclohexyl-3,3-dimethylcyclopentyldiethoxysilane, 3,5-dimethylcyclohexyl-3,3-dimethylcyclopentyldipropoxysilane, 3,3-dimethylcyclohexyl-3,3-dimethylcyclopentyldimethoxysilane, 4,4-dimethylcyclohexyl-3,3-dimethylcyclopentyldimethoxysilane, 3-chlorocyclohexylcyclopentyldimethoxysilane, 4-chlorocyclohexylcyclopentyldimethoxysilane, 3,5-dichlorocyclohexylcyclopentyldimethoxysilane, cyclohexyl-2-chlorocyclopentyldimethoxysilane, cyclohexyl-3-cyclopentyldimethoxysilane, cyclohexyl-2,3-dichlorocyclopentyldimethoxysilane, cyclohexyl-2,5-dichlorocyclopentyldimethoxysilane, 3-chlorocyclohexyl-2-chlorocyclopentyldimethoxysilane,4-chlorocyclohexyl-3-chlorocyclopentyldimethoxysilane, and 3,5-dichlorocyclohexyl-2,3-dichlorocyclopentyldimethoxysilane.

Preferred of these asymmetric organosilicon compounds are cyclohexylcyclopentyldimethoxysilane, cyclohexylcyclopentyldiethoxysilane, 3-methylcyclohexylcyclopentyldimethoxysilane, 4-methylcyclohexylcyclopentyldimethoxysilane, and 3,5-dimethylcyclohexylcyclopentyldimethoxysilane. These organosilicon compounds may be used either individually or in combination of two or more thereof.

In the present invention, an olefin is homo- or copolymerized in the presence of a catalyst comprising solid catalyst component (A), organoaluminum compound (B), and organosilicon compound (C). The ratio of components (A), (B), and (C) to be used is not particularly limited as long as the effects of the present invention are not impaired. Usually, organoaluminum compound (B) is used in an amount of from 1 to 500 mol and preferably from 5 to 400 mol per mol of the titanium atom in solid catalyst component (A), and organosilicon compound (C) is used in an amount of from 0.002 to 0.5 mol and preferably from 0.01 to 0.2 mol per mol of organobalunium compound (B).

The catalyst of the present invention can be prepared by bringing the above-described components (A), (B) and (C) into contact. There is no particular limitation on the order in contact of the components (A), (B) and (C). In general, the component (B) is brought into contact with the component (C) and subsequently with the component (A), or the component (B) is brought into contact with the component (A) and subsequently with the component (C).

Recommended combinations of the components (A), (B), and (C) are tabulated in Table 1 below.

TABLE 1

| Solid Catalyst Component (A) (Process of Preparation) | Organo-aluminum Compound (B) | Organosilicon Compound (C) |
| --- | --- | --- |
| process (7) | triethyl-aluminum | cyclohexylcyclopentyl-dimethoxysilane |
| process (7) | triethyl-aluminum | 3-methylcyclohexyl-cyclopentyldimethoxysilane |
| process (8) | triethyl-aluminum | cyclohexylcyclopentyl-dimethoxysilane |
| process (10) | triethyl-aluminum | cyclohexylcyclopentyl-dimethoxysilane |
| process (10) | triethyl-aluminum | 4-methylcyclohexyl-cyclopentyldimethoxysilane |
| process (12) | triethyl-aluminum | cyclohexylcyclopentyl-dimethoxysilane |
| process (12) | triethyl-aluminum | 3-methylcyclohexylcyclo-pentyldimethoxysilane |
| process (13) | triethyl-aluminum | cyclohexylcyclopentyl-dimethoxysilane |
| Process (13) | triethyl-aluminum | 3,5-dimethylcyclohexyl-cyclopentyldimethoxysilane |

Polymerization reaction according to the present invention may be carried out in the presence or absence of an organic solvent. The olefin monomer to be polymerized may be used in either a gaseous state or a liquid state. The polymerization is conducted at a temperature of not higher than 200° C., preferably not higher than 100° C., under a pressure of not higher than 10 MPa, preferably not higher than 5 MPa. The reaction may be effected either in a continuous system or in a batch system and through one step or two or more steps.

The olefins to be homo- or copolymerized according to the present invention are not particularly limited and generally have 2 to 20 carbon atoms, such as ethylene, propylene, 1-butene, 1-pentene, 4-methyl-1-pentene, and vinylcyclohexane. These olefins may be used either individually or in combination of two or more thereof. The effects of the present invention in assuring high stereoregularity, broad molecular weight distribution, and high yield are particularly pronounced in homopolymerization of propylene or copolymerization of propylene and ethylene.

For ensuring the improvements in catalytic activity and stereoregularity and particle properties of the polymer produced, it is preferable to conduct pre-polymerization prior to substantial polymerization. Monomers to be pre-polymerized include not only ethylene and propylene but other monomers, such as styrene and vinylcyclohexane.

The catalyst of the present invention is used in an amount of about 0.005 to 0.5mmol, preferably about 0.01 to 0.5 mmol, calculated as titanium atom in solid catalyst component (A) per liter of the polymerization zone.

According to the process of the present invention, the olefin polymers obtained have a broader molecular weight distribution than those obtained by conventional processes, by at least 1 higher as expressed in terms of the ratio of weight average molecular weight to number average molecular weight (Mw/Mn) of the olefin polymers, and the yield of stereoregular polymers is extremely high. That is, the process has been confirmed to provide polyolefins having not only broad molecular weight distribution (for example, 6 or higher in terms of the Mw/Mn) but high stereoregularity in extremely high yield.

The present invention will now be illustrated in greater detail with reference to Examples in view of Comparative Examples, but it should be understood that the present invention is not construed as being limited to these Examples. All the percents are by weight unless otherwise indicated.

EXAMPLE 1

Preparation of Solid Catalyst Component (A-1):

In a 200 ml-volume round flask equipped with a stirrer having been thoroughly purged with nitrogen gas were charged 10 g of diethoxymagnesium and 80 ml of toluene to prepare a suspension. To the suspension was added 20 ml of titanium tetrachloride, the mixture was heated to 80° C., at which 2.7 ml of di-n-butyl phthalate was added. The mixture was further heated up to 110° C., at which the mixture was allowed to react for 2 hours with stirring. After completion of the reaction, the reaction mixture was washed with two 100 ml portions of toluene at 90° C., and 20 ml of titanium tetrachloride and 80 ml of toluene were added thereto. The mixture was heated to 100° C., at which it was allowed to react for 2 hours while stirring. After completion of the reaction, the reaction mixture was washed with ten 100 ml portions of n-heptane at 40° C. to obtain solid catalyst component (A-1). The solid content of solid catalyst component (A-1), separated by solid-liquid separation, was found to have a titanium content of 2.91%.

Preparation of Catalyst System and Polymerization:

In a 2.0 l-volume autoclave equipped with a stirrer having been thoroughly purged with nitrogen gas were charged 1.32 mmol of triethylaluminum, 0.13 mmol of cyclohexylcyclopentyldimethoxysilane, and 0.0066 mmol, in terms of titanium atom, of the above prepared solid catalyst component (A-1) to form a catalyst system for polymerization. Then, 1.8 l of hydrogen gas and 1.4 l of liquefied propylene were charged in the autoclave, and the system was subjected to polymerization at 70° C. for 30 minutes. The properties of the resulting polymer are shown in Table 2 below. In Table 2, n-heptane-insoluble content, polymerization activity, yield of total crystalline polymer, and molecular weight distribution were obtained as follows.

n-Heptane-Insoluble Content:

The polymer as produced weighing (a) g was extracted with boiling n-heptane for 6 hours, and the weight of the insoluble polymer (referred to (b) g) was measured.

Polymerization Activity:

(a)/Weight of solid catalyst component (g)

Yield of Total Crystalline Polymer:

((b)/(a)) × 100 (%)

Molecular Weight Distribution:

Mw/Mn

Mw: Weight average molecular weight

Mn: Number average molecular weight

EXAMPLE 2

Preparation of Solid Catalyst Component (A-2):

In a 200 ml-volume round flask equipped with a stirrer having been thoroughly purged with nitrogen gas were charged 20 ml of titanium tetrachloride and 30 ml of toluene to prepare a mixed solution. To the mixed solution was added a suspension of 10 g of spherical diethoxymagnesium particles (length/width=1.1/1; average particle size 30μm; ln($D_{90}D_{10}$)=1.23), 50 ml of toluene, and 3.6 ml of di-n-butyl phthalate, and the mixture was heated to 90° C., at which it was allowed to react for 1 hour with stirring. After completion of the reaction, the reaction mixture was washed with two 100 ml portions of toluene at 90° C., and 20 ml of titanium tetrachloride and 80 ml of toluene were added thereto. The mixture was heated to 110° C., at which it was allowed to react for 2 hours while stirring. After completion of the reaction, the reaction mixture was washed ten 100 ml portions of n-heptane at 40° C. to obtain solid catalyst component (A-2). The solid content of catalyst component (A-2), separated by solid-liquid separation, was found to have a titanium content of 2.87%.

Preparation of Catalyst System and Polymerization:

Propylene was polymerized in the same manner as in Example 1, except for using solid catalyst component (A-2). The reaction results are shown in Table 2.

EXAMPLE 3

Preparation of Solid Catalyst Component (A-3):

In a 200 ml-volume round flask equipped with a stirrer having been thoroughly purged with nitrogen gas were charged 10 g of diethoxymagnesium and 80 ml of toluene to prepare a suspension. To the suspension was added 20 ml of titanium tetrachloride, and the mixture was heated to 60° C., at which 1.0 ml of diethyl phthalate was added. The mixture was further heated up to 110° C., at which 2.5 ml of di-iso-octyl phthalate was added thereto. The mixture was further heated to 112° C., at which the mixture was allowed to react for 1.5 hours with stirring. After completion of the reaction, the reaction mixture was washed with two 100 ml portions of toluene at 90° C., and 20 ml of titanium tetrachloride and 80 ml of toluene were added thereto. The mixture was heated to 100° C., and it was allowed to react at that temperature for 2 hours while stirring. After completion of the reaction, the reaction mixture was washed with ten 100 ml portions of n-heptane at 40° C. to obtain solid catalyst component (A-3). The solid content of solid catalyst component (A-3), separated by solid-liquid separation, was found to have a titanium content of 2.74%.

Preparation of Catalyst System and Polymerization:

Propylene was polymerized in the same manner as in Example 1, except for using solid catalyst component (A-3). The reaction results are shown in Table 2.

EXAMPLE 4

Preparation of Solid Catalyst Component (A-4):

In a 200 ml-volume round flask equipped with a stirrer having been thoroughly purged with nitrogen gas were charged 10 g of diethoxymagnesium and 80 ml of toluene to prepare a suspension. To the suspension was added 20 ml of titanium tetrachloride, and the mixture was heated to 62° C., at which 1.0 ml of diethyl phthalate was added. The mixture was heated up to 110° C., at which 4.0 ml of di-iso-octyl phthalate was added thereto. The mixture was further heated to 112° C., at which the mixture was allowed to react for 1.5 hours with stirring. After completion of the reaction, the reaction mixture was washed with two 100 ml portions of toluene at 90° C., and 20 ml of titanium tetrachloride and 80 ml of toluene were added thereto. The mixture was heated to 100° C., and it was allowed to react at that temperature for 2 hours while stirring. After completion of the reaction, the reaction mixture was washed with ten 100 ml portions of n-heptane at 40° C. to obtain solid catalyst component (A-4). The solid content of solid catalyst component (A-4), separated by solid-liquid separation, was found to have a titanium content of 2.17%.

Preparation of Catalyst System and Polymerization:

Propylene was polymerized in the same manner as in Example 1, except for using solid catalyst component (A-4). The reaction results are shown in Table 2.

COMPARATIVE EXAMPLE 1

Propylene was polymerized in the same manner as in Example 1, except for replacing cyclohexylcyclopentyldimethoxysilane with phenyltriethoxysilane. The reaction results are shown in Table 2.

COMPARATIVE EXAMPLE 2

Propylene was polymerized in the same manner as in Example 1, except for replacing cyclohexylcyclopentyldimethoxysilane with cyclohexylmethyldimethoxysilane. The reaction results are shown in Table 2.

COMPARATIVE EXAMPLE 3

Propylene was polymerized in the same manner as in Example 1, except for replacing cyclohexylcyclopentyldimethoxysilane with dicyclopentyldimethoxysilane. The reaction results are shown in Table 2.

EXAMPLE 5

Preparation of Solid Catalyst Component (A-5):

In a 200 ml-volume round flask equipped with a stirrer having been thoroughly purged with nitrogen gas were charged 7.14 g of anhydrous magnesium chloride, 37.5 ml of decane and 35.1 ml of 2-ethylhexyl alcohol, and the resulting mixture was heated at 130° C. for 2 hours to obtain a uniform solution. Then 1.67 g of phthalic anhydride was added thereto, followed by stirring at 130° C. for one hour. The thus obtained uniform solution was cooled to room temperature and was dropwise added, over one hour, to 200 ml of titanium tetrachloride which had been cooled at −20° C. After addition of the solution, the temperature of the resulting solution was increased to 110° C. over 4 hours, at which 5.03 ml of diisobutyl terephthalate was further added to the solution, and the resulting solution was then stirred for 2 hours to continue the reaction at 110° C. The hot reaction mixture was subjected to filtration to thereby obtain a solid product which was then dispersed in 275 ml of titanium tetrachloride and allowed to stand at 110° C. for 2 hours. Thereafter, a solid product was separated again from the dispersion by filtration while the dispersion was hot, and the solid product was washed with decane and heptane at 110° C. to obtain solid catalyst component (A-5). The solid content of solid catalyst component (A-5), separated by solid-liquid separation, was found to have a titanium content of 2.06 %.

Preparation of Catalyst System and Polymerization:

Propylene was polymerized in the same manner as in Example 1, except for using solid catalyst component (A-5). The reaction results are shown in Table 2.

EXAMPLE 6

Preparation of Solid Catalyst Component (A-6)

In a 250 ml-volume round flask equipped with a stirrer having been thoroughly purged with nitrogen gas was charged a solution of 1.4 ml of titanium tetrachloride dissolved in 74 ml of chlorobenzene, and 3.6 ml of diisobutyl phthalate and 11.8 g of diethoxymagnesium were subsequently added thereto. To the resulting solution was further added a solution of 94 ml of titanium tetrachloride dissolved in 24 ml of chlorobenzene. The addition of these compounds and the solution was conducted at a temperature of 20 to 25 ° C. The resulting mixture was heated at 110 ° C. with stirring for one hour, followed by filtration while the mixture was hot. The thus obtained solid product was added to a solution of 94 ml of titanium tetrachloride dissolved in 24 ml of chlorobenzene to form a slurry at room temperature. Then, a solution obtained by dissolving 0.9 g of phthaloyl dichloride in 74 ml of chlorobenzene was added to the slurry at room temperature, followed by heating at 110 ° C. with stirring for 30 minutes. The resulting mixture was filtered while it was hot, whereby a solid product was obtained.

To the thus obtained solid product was added, at room temperature, a solution of 94 ml of titanium tetrachloride dissolved in 24 ml of chlorobenzene to thereby form a slurry. 74 ml of chlorobenzene was further added, at room temperature, to the slurry which was then heated at 110 ° C. with stirring for 30 minutes. The resulting mixture was filtered while it was hot, whereby a solid product was obtained. Using the thus obtained solid product, the above procedure was repeated again to obtain a solid product, which was then washed 10 times with 100 ml of heptane at 25° C. Thus, solid catalyst component (A-6) was obtained. The solid content thereof, separated by solid-liquid separation, was found to have a titanium content of 2.63 %.

Preparation of Catalyst system and Polymerization:

Propylene was polymerized in the same manner as in Example 1, except for using solid catalyst component (A-6). The reaction results are shown in Table 2.

COMPARATIVE EXAMPLE 4

Propylene was polymerized in the same manner as in Example 5, except for replacing cyclohexylcyclopentyldimethoxysilane with cyclohexylmethyldimethoxysilane. The reaction results are shown in Table 2.

COMPARATIVE EXAMPLE 5

Propylene was polymerized in the same manner as in Example 6, except for replacing cyclohexylcyclopentyldimethoxysilane with cyclohexylmethyldimethoxysilane. The reaction results are shown in Table 2.

TABLE 2

| Example No. | Weight of Polymer Produced (g) | n-Heptane Insoluble Content (g) | Polymerization Activity (g/g-cat.) | Yield of Total Crystalline Polymer (%) | MI (g/10 min) | Molecular Weight Distribution |
|---|---|---|---|---|---|---|
| Example 1 | 306.4 | 302.3 | 28,200 | 98.7 | 5.0 | 7.0 |
| Example 2 | 339.5 | 334.4 | 30,800 | 98.5 | 3.0 | 6.5 |
| Example 3 | 293.1 | 289.0 | 25,500 | 98.6 | 3.6 | 7.1 |
| Example 4 | 349.1 | 343.2 | 23,900 | 98.3 | 3.6 | 7.1 |
| Example 5 | 177.1 | 173.9 | 23,100 | 98.2 | 4.5 | 6.5 |
| Example 6 | 217.1 | 215.6 | 36,200 | 99.3 | 3.7 | 6.4 |
| Comp. Example 1 | 220.7 | 217.6 | 20,300 | 98.6 | 10.0 | 5.2 |
| Comp. Example 2 | 322.7 | 317.5 | 29,700 | 98.4 | 5.0 | 5.4 |
| Comp. Example 3 | 385.7 | 380.7 | 35,500 | 98.7 | 2.5 | 4.9 |
| Comp. Example 4 | 192.3 | 188.8 | 25,100 | 98.2 | 5.2 | 5.2 |
| Comp. Example 5 | 215.9 | 211.4 | 36,000 | 97.9 | 5.0 | 5.1 |

The catalyst for olefin polymerization according to the present invention comprises (A) a specific solid catalyst component, (B) an organoaluminum compound, and (C) an asymmetric organosilicon compound containing a cyclohexyl group or a derivative thereof and a cyclopentyl group or a derivative thereof. Polymerization of an olefin in the presence of the catalyst of the present invention provides an olefin polymer having high stereoregularity (high yield of total crystalline polymer) and broad molecular weight distribution in high yield.

While the invention has been described in detail and with reference to specific examples thereof, it will be apparent to one skilled in the art that various changes and modifications can be made therein without departing from the spirit and scope thereof.

What is claimed is:

1. A catalyst for the polymerization of olefins comprising (A) a solid catalyst comprising magnesium, titanium, an electron donor compound, and a halogen which is prepared by bringing metallic magnesium or a magnesium compound, a titanium halide compound, and an electron donor compound into contact, (B) an organoaluminum compound, and (C) an organosilicon compound represented by formula (I):

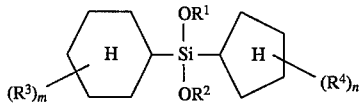

(I)

wherein $R^1$ and $R^2$, which may be the same or different, each represents an alkyl group having from 1 to 3 carbon atoms; $R^3$ and $R^4$, which may be the same or different, each represents an alkyl group having from 1 to 3 carbon atoms, or a halogen atom; and m and n each represents 0 or an integer of 1 or 2.

2. The catalyst for the polymerization of olefins as claimed in claim 1, wherein said magnesium compound used in preparation of solid catalyst component (A) is a dialkoxymagnesium.

3. The catalyst for the polymerization of olefins as claimed in claim 1, wherein said magnesium compound used in preparation of solid catalyst component (A) is diethoxymagnesium.

4. The catalyst for the polymerization of olefins as claimed in claim 1, wherein said magnesium compound used in preparation of solid catalyst component (A) is diethoxymagnesium in the form of spherical particles.

5. The catalyst for the polymerization of olefins as claimed in claim 1, wherein said titanium halide compound used in preparation of solid catalyst component (A) is a titanium halide or alkoxytitanium halide, represented by formula $Ti(OR^5)_n X_{4-n}$, wherein $R^5$ represents an alkyl group having from 1 to 4 carbon atoms, X represents a chlorine atom, a bromide atom or an iodine atom, and n is 0 or an integer of 1, 2 or 3.

6. The catalyst for the polymerization of olefins as claimed in claim 1, wherein said electron donor compound used in preparation of solid catalyst component (A) is a diester of phthalic acid, the ester moieties thereof being an alkyl group having 1 to 10 carbon atoms.

7. The catalyst for the polymerization of olefins as claimed in claim 1, wherein said organoaluminium compound (B) is represented by formula $R^7 yAlY_{3-y}$, wherein $R^7$ represents an alkyl group having from 1 to 4 carbon atoms, Y represents a hydrogen atom, a chlorine atom, a bromine atom, or an iodine atom, and y represents an integer of 1, 2 or 3.

8. The catalyst for the polymerization of olefins as claimed in claim 1, wherein said organosilicon compound (C) is at least one compound selected from the group consisting of cyclohexylcyclopentyldimethoxysilane, cyclohexylcyclopentyldiethoxysilane, 3-methylcyclohexylcyclopentyldimethoxysilane, 4-methylcyclohexylcyclopentyldimethoxysilane and 3,5-dimethylcyclohexylcyclopentyldimethoxysilane.

9. The catalyst as claimed in claim 1, wherein said component (A) solid catalyst consists essentially of magnesium, titanium, and electron donor compound and a halogen, which solid catalyst is prepared by bringing metallic magnesium or a magnesium compound, a titanium halide compound and an electron donor compound into contact.

* * * * *